US006103771A

United States Patent [19]

Galer et al.

[11] Patent Number: 6,103,771
[45] Date of Patent: Aug. 15, 2000

[54] METHOD OF TREATING NEUROMA PAIN

[75] Inventors: Bradley S. Galer, Seattle, Wash.;
Larry J. Caldwell, San Jose, Calif.

[73] Assignee: Caldwell Galer Incorporated, San Jose, Calif.

[21] Appl. No.: 09/045,285

[22] Filed: Mar. 20, 1998

[51] Int. Cl.[7] .................................................. A61K 31/00
[52] U.S. Cl. ......................... 514/817; 514/818; 424/443; 424/445; 424/446; 424/447; 424/449
[58] Field of Search ................................... 424/443, 445, 424/446, 447, 449; 514/817, 818

[56] References Cited

U.S. PATENT DOCUMENTS

| | | | |
|---|---|---|---|
| 4,440,777 | 4/1984 | Zupan | 424/274 |
| 4,560,553 | 12/1985 | Zupan | 424/78 |
| 4,588,580 | 5/1986 | Gale et al. | 424/21 |
| 4,911,707 | 3/1990 | Heiber et al. | 424/449 |
| 4,963,591 | 10/1990 | Fourman et al. | 514/944 |
| 5,069,909 | 12/1991 | Sharma et al. | 424/449 |
| 5,070,084 | 12/1991 | Campbell | 514/248 |
| 5,079,008 | 1/1992 | Sinnreich et al. | 424/448 |
| 5,330,452 | 7/1994 | Zook | 604/307 |
| 5,368,860 | 11/1994 | Sunami et al. | 424/448 |
| 5,401,728 | 3/1995 | Simon | 514/78 |
| 5,543,148 | 8/1996 | Lapidus | 424/401 |
| 5,613,958 | 3/1997 | Kochinke et al. | 604/307 |
| 5,665,378 | 9/1997 | Davis et al. | 424/448 |
| 5,667,719 | 9/1997 | Caldwell et al. | 424/449 |

FOREIGN PATENT DOCUMENTS 0 399 432 A2  11/1990  European Pat. Off. .

OTHER PUBLICATIONS

CAPLUS DN 115:105951, Rumsfield et al., DICP, Ann. Pharmacother., (1991), 25(4), 381–7, (abstract).

Rumsfield et al., DICP, The Annals of Pharmacotherapy, vol. 25, Apr. 1991, 381–387.

Rowbotham et al., Pain, vol. 65, 1996, 39–44.

Dini et al., Pain (Aug. 1993)54:223–6. (abstract only).

Watson & Evans, Pain (Dec. 1992) 51:375–379, (abstract only).

Watson et al., Pain (Aug. 1989) 38:177–86. (abstract only).

Alexander, Ian J. et al., "Morton's Neuroma: A Review of Recent Concepts," *Orthopedics* (Jan. 1987) vol. 10, No. (1):103–106.

Kittrelle, Jeffrey P. et al., "Cluster Headache Local Anesthetic Abortive Agents," *Arch Neurol* (May 1985) vol. 42:496–498.

Medicino, Samuel S. et al., "Morton's Neuroma update on Diagnosis and Imaging," *Clinics In Podiatric Medicine and Surgery* (Apr. 1997) vol. 14, No. (2):303–311.

Nunan, Patrick J. et al., "Management of Morton's Neuroma In Athlete's," *Clinics In Podiatric Medicine and Surgery* (Jul. 1997) vol. 14, No.(3):489–501.

Wu, Kent K., "Morton's Interdigital Neuroma: A Clinical Review of Its Etiology, Treatment, and Results," *The Journal of Foot and Ankle Surgery* (1996) vol. 35, No. (2):112–119.

*Primary Examiner*—Dwayne C. Jones
*Assistant Examiner*—C. Delacroix-Muirheid
*Attorney, Agent, or Firm*—Bret Field; Bozicevic, Field & Francis LLP

[57] ABSTRACT

Methods of treating a host suffering from neuroma pain are provided. In the subject methods, a topical local anesthetic composition is applied to a keratinized skin site of the host proximal to the neuroma responsible for the neuroma pain. Preferably, the topical local anesthetic composition comprises eucalyptol in addition to an effective amount of a local anesthetic. The subject methods find particular use in the treatment of pain associated with Morton's neuroma.

13 Claims, No Drawings

METHOD OF TREATING NEUROMA PAIN

TECHNICAL FIELD

The field of this invention is the treatment of neuroma pain.

BACKGROUND OF THE INVENTION

Neuromas, i.e. focal abnormal bundles of nerves under the skin, may result in presence of chronic pain. Neuromas may result from repetitive blunt injury to a nerve, such as in "Morton's Neuroma" which results due to chronic running or dancing, as well as following direct transection of a sensory nerve, such as those neuromas with amputation and the subsequent development of "neuroma stump" pain.

Current medical treatment options of neuroma pain are limited. One method employed to treat neuroma pain involves the direct injection of a steroid, with or without a local anesthetic, into the neuroma to achieve an invasive nerve block. Such nerve blocks tend to provide only transitory relief. Furthermore, such nerve blocks require physician visits, are invasive and can be painful. In addition, complications can arise from long term steroid use associated with such methods. Other treatment options include surgical transection and removal of the neuroma. While effective in removing the painful neuroma, new painful neuromas frequently form at the surgical site within a relatively short time following surgery. In addition, surgery is not always desirable because of its invasive nature, potential for complications, and expense. Yet other treatment methodologies include the use of orthotic devices. However, such devices rarely provide long-term pain relief.

Therefore, there is a continued need for the identification of new methods for treating neuroma pain. Ideally, such methods should be simple enough to be self-administered, be suitable for chronic use and afford effective relief from neuroma pain.

Relevant Literature

References providing a review of neuromas and methods for their treatment, particularly Morton's neuroma, include: Nunan & Giesy, Clinics in Podiatric Medicine and Surgery (July 1997) 14: 489–501; Mendicino & Rockett, Clinics in Podiatric Medicine and Surgery (April 1997) 14: 303–311; Wu, J. Foot Ankle Surg. (March 1996) 35: 112–119; and Alexander et al., Orthopedics (January 1987) 10:103–106.

SUMMARY OF THE INVENTION

Methods for treating a host suffering from neuroma pain are provided. In the subject methods, a topical local anesthetic composition is applied to a keratinized skin site of a host proximal to the underlying neuroma responsible for the neuroma pain. The composition preferably includes, in addition to an effective amount of a local anesthetic, eucalyptol. The subject methods find particular application in the treatment of pain associated with Morton's neuroma.

DESCRIPTION OF THE SPECIFIC EMBODIMENTS

Methods are provided for at least reducing the pain experienced by a host having a neuroma. In the subject methods, a topical local anesthetic composition comprising an effective amount of a local anesthetic is applied to a keratinized skin site of the host in a region proximal to the neuroma. The subject methods find particular use in the treatment of a host suffering from pain associated with Morton's neuroma.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Topical compositions employed in the subject method will include a local anesthetic as the active agent. Although two or more local anesthetic agents may be present in the subject compositions, generally the subject compositions will comprise a single local anesthetic agent. The local anesthetic employed in the subject methods will be an anesthetic which, when administered in the topical formulations, rapidly penetrates a keratinized skin surface to reduce abnormal ectopic neuronal discharges in the neuroma's nerves underlying the skin surface. The local anesthetic will have a molecular weight and melting point that is compatible with transport across the keratinized skin surface. Generally, the molecular weight of the local anesthetic will not exceed about 300 dal, and will more usually not exceed about 250 dal. The melting point of the local anesthetic will be less than about 100° C. In many embodiments, the local anesthetic will be a compound comprised of a secondary or tertiary amine linked by a bond or through a connecting group to an aromatic group. The local anesthetic will generally be an alkanyl compound of from about 9 to 20 carbon atoms. Because the composition is applied topically, the local anesthetic will generally be present in the composition as a free base to promote penetration of the agent through the skin surface. A large number of local anesthetics are known in the art, many of which are suitable for topical application. Suitable local anesthetics include lidocaine, butamben, butanilicaine, ethyl aminobenzoate, fornocaine, hydroxyprocaine, isobutyl p-aminobenzoate, naepaine, octacaine, parethoxycaine, piridocaine, prilocaine, procaine, risocaine, tolycaine, trimecaine, particularly ethylaminobenzoate (benzocaine). The amount of local anesthetic present in the subject compositions will be sufficient to provide an effective amount of the agent when topically administered according to the subject methods. The precise amount of anesthetic agent present in the topical formulation will depend on the particular agent employed, but will generally range from about 5 to 50% by weight, usually from about 10 to 40% by weight.

In preferred embodiments of the subject invention, the topical applications employed in the subject methods contain eucalyptol, which serves as a penetration enhancing agent for the local anesthetic. Eucalyptol (1,3,3-trimethyl-2-oxabicyclo [2,2,2]-octane) is the chief constituent of oil of eucalyptus and is also known as cineole and cajeputol. Eucalyptol is known in the art, having found use as an insect repellant and as a flavoring agent. The amount of eucalyptol present in the composition will range from about 10 to 80%, usually from about 10 to 50% by weight, and more usually from about 20 to 40% by weight of the composition.

Optionally, the topical compositions employed in the subject methods may further comprise one or more additional penetration enhancing agents which work in combination with the eucalyptol to provide for rapid penetration of the local anesthetic. Additional penetration enhancing agents will be capable of rapid penetration of the skin and be pharmaceutically acceptable, i.e. non-toxic to the host at the levels at which they are present in the composition.

Examples of additional penetration enhancing agents which may find use in the subject compositions include: propylene glycol and N-methyl-2-pyrrolidone. An additional penetration enhancing agent that finds particular use in combination with eucalyptol in the subject compositions is N,N-diethyl-m-toluamide (DEET). When present, the amount of this additional penetration enhancing agent in the subject compositions will vary depending on the particular agent, as well as the local anesthetic present in the composition. The amount of additional penetration enhancing agent or agents in the subject compositions will range from 10 to 80% by weight, usually from about 30 to 60% by weight. Generally, the ratio of eucalyptol to additional penetration enhancing agent in the subject compositions will be from 0.25:1 to 2:1, and will usually be from about 1:2 to 1:1.

The compositions comprising the local anesthetic, eucalyptol and any additional penetration enhancing agent employed in the subject methods will be formulated in a manner convenient for topical application. Thus, the subject compositions may be formulated as stable solutions or suspensions of the local anesthetic in eucalyptol. Alternatively, the local anesthetic and eucalyptol may be combined with one or more carrier materials to form a solution, suspension, gel, lotion, cream, ointment, aerosol spray or the like, as in known in the art.

Gel vehicles in which the subject local anesthetic and eucalyptol may be formulated to produce a topical application useful in the subject methods are physiologically acceptable and are generally comprise a solvent in combination with a thickening agent. The solvent will generally be an alkanol, such as an alcohol or polyol, including: ethanol, isopropanol, propylene glycol, glycerol, and the like. These alcohols and polyols may be used individually or in combination. In the gel vehicle, the solvent will generally be present in from about 1 to 80 weight %, more commonly 10 to 40 weight % of the topical composition.

Conventional gelling or thickening agents may be employed to provide for a formulation which can be conveniently applied to the skin. Gelling agents which have been found to be effective and are illustrative of conventionally used gelling agents for skin application include Carbomer 940 (neutralized with diisopropanolamine), neutralized polyacrylic acid, etc. The gelling agent will be used in an amount sufficient to provide the appropriate viscosity, generally being in the range of about 0.1–5 weight percent of the formulation.

Non-ionic surfactants may be included in the compositions, where the nonionic surfactants may serve as cosolvents and epidermal penetration enhancers, in addition to the eucalyptol and any optional penetration enhancing agent described above. Conventional surfactants may be employed, which are physiologically acceptable, such as sorbitan esters, etc. When present, the nonionic surfactant will generally be present in an amount of from about 2–20 weight percent of the formulation.

The topical composition may also contain other physiologically acceptable excipients or other minor additives, particularly associated with organoleptic properties, such as fragrances, dyes, emulsifiers, buffers, cooling agents (e.g. menthol), antibiotics, stabilizers or the like. The excipients and minor additives will be present in conventional amounts ranging from about 0.001% to 5%, more commonly 0.001–2%, by weight, usually not exceeding a total of 10% by weight.

Where convenient, e.g. with a gel formulation, the topical application may be covered with an occlusive dressing, which may be porous or non-porous, so as to protect the gel from mechanical removal during the period of treatment. Various inert coverings may be employed, which include the various materials which may find use in plasters, described below. Alternatively, non-woven or woven coverings may be employed, particularly elastomeric coverings, which allow for heat and vapor transport. These coverings allow for cooling of the pain site, which provides for greater comfort, while protecting the gel from mechanical removal.

Instead of a gel, a plaster may be employed, where the composition comprising the local anesthetic and eucalyptol, and any additional penetration enhancers, may be formulated into the adhesive of the plaster. In the case of plasters, the coverings may include polyvinyl chloride, polyvinylidene chloride, (SARAN®), polyethylene, synthetic rubber, woven or nonwoven polyester fabric, etc. The local anesthetic and the eucalyptol may be combined with the adhesive with the aid of a cosolvent, or a combination of cosolvents, such as propylene glycol, glycerin, methyl salicylate, glycol salicylate, or the like. The particular choice of adhesive is not critical, there being a wide variety of physiologically acceptable adhesives, which can maintain the local anesthetic, eucalyptol and any additional penetration enhancing agent, in contact with the skin.

Of particular interest are the topical local anesthetic compositions described in U.S. Pat. No. 4,440,777, the disclosure of which is herein incorporated by reference.

In the subject methods, the topical composition comprising the local anesthetic is applied to a keratinized skin site of the host proximal to neuroma, where the term neuroma is used to refer to a painful focal bundle of nerves and/or enlargement of nerves. The neuroma may be present in a variety of body locations, including at an interdigital site as in Morton's neuroma, at a site proximal to amputation, and the like. The skin site at which the composition is applied will be sufficiently proximal to the neuroma target nerves, e.g. the skin site overlies the region innervated by the neuroma target nerves, so that upon contact of the composition with the skin surface, the local anesthetic can readily reach the neuroma target nerves and exert its activity. The particular skin site to which the topical composition is applied will necessarily depend on the location of the neuroma. For example, in treating interdigital neuromas, the topical composition will be applied to the interdigital region of the foot directly above or below, usually above the neuroma site. The distance between the neuroma and site of administration should not exceed about 3 cm and preferably should not exceed about 1 cm.

The subject compositions are applied to the skin site for a period of time ranging from 0.25 to 6 hours, usually from about 0.5 to 5 hours, during which time the host experiences relief from pain due to the activity of the local anesthetic on the neuroma target nerves. If neuroma pain recurs following removal of the topical composition, a new topical composition may be applied. The process may be repeated as necessary and desired to achieve pain relief. Because of the nature of the topical local anesthetic composition employed in the subject methods, penetration of the local anesthetic is rapid. Therefore, the patient experiences relief from the pain shortly after application. Usually the patient will experience at least some relief from the pain about 0.25 to 30 min following application of the topical composition, usually about 5 to 30 min following application of the topical composition.

The amount of composition applied will usually be sufficient to cover a majority of the region of skin overlying the neuroma target nerves to ensure that conduction in a sufficient percentage of the neuroma target nerves is blocked, so that the host experiences pain relief. The exact amount of topical composition that is applied may be determined empirically. For example, where the topical application is applied to the interdigital region of the foot, the amount of composition applied will be sufficient to cover at least about 50%, more usually at least about 75% of the region. For solutions, dispersions, gels, lotions, creams and the like, the composition will be spread over the region and a covering optionally applied thereto. For patches, an appropriate sized patch will be placed over the region comprising the skin site.

Conveniently, the composition may be provided in a unit dosage format, which formats are known in the art.

Upon application of the topical composition, the local anesthetic rapidly penetrates the surface of the skin and reduces the abnormal ectopic neuronal discharges in the neuroma target nerves which are proximal to the skin site. As a result, the patient experiences a t least a partial subsidence in the intensity of pain, and in some cases may experience a complete cessation of pain. Thus, application of the topical local anesthetic compositions in accordance with the subject methods results in treatment of the host suffering from pain.

A variety of hosts are treatable according to the subject methods. Generally such hosts are "mammals" or "mammalian," where these terms are used broadly to describe organisms which are within the class mammalia. Of particular interest is the treatment of primates with the subject methods, (e.g., humans, chimpanzees, and monkeys), where the subject methods are particularly suited for use in the treatment of humans suffering from neuroma pain.

Kits with unit doses of the topical formulation used in the subject methods, are provided. In such kits, in addition to the containers containing the unit doses will be an informational package insert describing the use and attendant benefits of the drugs in treating pathological condition of interest.

The following examples are offered by way of illustration and not by way of limitation.

EXPERIMENTAL

The patient was a 32 year old woman who had been diagnosed 10 years earlier with a Morton's Neuroma. Following many years of dance, she had developed disabling pain localized to the plantar surface of her foot after activities that required her to be on her feet for an extended period of time or those activites requiring rapid and quick movements of her feet, such as dance or athletic events. She had been evaluated by 3 podiatrists and one orthopedic surgeon in the past, all of whom diagnosed a "Morton's Neuroma." Prior treatments had included: 3 cortisone/local anesthetic injections which were painful when administered and provided partial transient pain relief. She was given orthotics which do provide partial relief when worn; however, she is not able to wear these orthotics when dancing or doing certain athletic events since they do not fit in these activity-specific shoes.

After playing soccer for several hours, the patient developed her typical symptoms of Morton's Neuroma, severe, sharp, burning pain localized to her foot, which caused her to get off her feet. She then applied a topical local anesthetic composition (33% benzocaine, 44% DEET, 23% eucalyptol) directly to her painful skin overlying the neuroma. Within 10 minutes she had complete resolution of her pain. Pain relief lasted several hours and she was able to walk on her foot without any resultant pain. The following day, she again applied the topical medication to the skin overlying the neuroma prior after playing several hours of soccer. Again, she reported complete pain relief starting 10 minutes after application, which lasted for several hours with the ability to walk on her foot without pain.

It is evident from the above results and discussion that the subject methods provide a relatively rapid, complete and simple means of treating neuroma pain. Because the methods are so simple, they can be self administered, providing for distinct advantages of methodologies requiring health care professional involvement. Furthermore, because extremely low (clinically ineffective) doses of the medication enter the bloodstream, there are no systemic side-effects.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for at least reducing the intensity of pain resulting from a Morton's neuroma, said method comprising:

applying a topical local anesthetic composition comprising an effective amount of a local anesthetic to a keratinized skin site proximal to said Morton's neuroma.

2. The method according to claim 1, wherein said topical local anesthetic composition comprises eucalyptol.

3. The method according to claim 2, wherein said composition further comprises an additional penetration enhancing agent.

4. A method for treating a host suffering from neuroma pain from a Morton's neuroma, said method comprising:

applying a topical local anesthetic composition comprising an effective amount of a local anesthetic to a keratinized skin site of said host, wherein said skin site is proximal to the neuroma responsible for said neuroma pain from said Morton's neuroma.

5. The method according to claim 4, wherein said topical local anesthetic composition comprises eucalyptol.

6. The method according to claim 5, wherein said composition further comprises an additional penetration enhancing agent.

7. The method according to claim 4, wherein said local anesthetic has a molecular weight that does not exceed about 300 daltons.

8. The method according to claim 7, wherein said local anesthetic comprises from about 9 to 20 carbon atoms.

9. A method for treating a host suffering from pain resulting from Morton's neuroma, said method comprising:

applying a topical local anesthetic composition to a keratinized skin site of said host proximal to said Morton's neuroma, wherein said composition comprises an effective amount of a local anesthetic and eucalyptol.

10. The method according to claim 9, wherein said host is a human.

11. The method according to claim 10, wherein said composition further comprises an additional penetration enhancing agent.

12. The method according to claim 10, wherein said local anesthetic has a molecular weight that does not exceed about 300 daltons.

13. The method according to claim 12, wherein said local anesthetic comprises from about 9 to 20 carbon atoms.

* * * * *